United States Patent [19]
Felder et al.

[11] Patent Number: 5,733,528
[45] Date of Patent: Mar. 31, 1998

[54] PARAMAGNETIC CHELATES FOR NUCLEAR MAGNETIC RESONANCE DIAGNOSIS

[75] Inventors: Ernst Felder, Riva S. Vitale, Switzerland; Pier Lucio Anelli; Mario Virtuani, both of Milan, Italy; Andrea Beltrami, Mandello Del Lario, Italy; Marco Lolli, Milan, Italy

[73] Assignee: Dibra S.p.A., Milan, Italy

[21] Appl. No.: 448,477

[22] PCT Filed: Nov. 25, 1994

[86] PCT No.: PCT/EP94/03906

§ 371 Date: May 30, 1995

§ 102(e) Date: May 30, 1995

[87] PCT Pub. No.: WO95/15319

PCT Pub. Date: Jun. 8, 1995

[30] Foreign Application Priority Data

Dec. 3, 1993 [CH] Switzerland ............ MI93A2541
Oct. 26, 1994 [CH] Switzerland ............ MI94A2188

[51] Int. Cl.$^6$ .................. A61K 49/00; G01N 31/00; G01N 33/48

[52] U.S. Cl. ............ 424/9.365; 562/400; 540/1; 424/1.11; 424/1.65; 534/10

[58] Field of Search ................ 424/1.11, 1.65, 424/1.77, 9.1, 9.3, 9.36, 9.37, 9.361, 9.364, 9.365, 9.4, 9.42, 9.5; 534/10–16; 540/1; 556/1–5; 562/400

[56] References Cited

U.S. PATENT DOCUMENTS

| | | | |
|---|---|---|---|
| 4,647,447 | 3/1987 | Gries et al. | 424/9.1 |
| 4,885,363 | 12/1989 | Tweedle et al. | 424/9.1 |
| 4,957,939 | 9/1990 | Gries et al. | 424/9.1 |
| 4,963,344 | 10/1990 | Gries et al. | 424/9.1 |
| 5,021,236 | 6/1991 | Gries et al. | 424/9.1 |
| 5,256,395 | 10/1993 | Barbet et al. | 424/1.11 |
| 5,362,475 | 11/1994 | Gries et al. | 424/9.1 |
| 5,482,700 | 1/1996 | Deutsch et al. | 424/9.364 |
| 5,560,903 | 10/1996 | Gries et al. | 424/9.36 |

FOREIGN PATENT DOCUMENTS

| | | |
|---|---|---|
| 0230893 | 5/1987 | European Pat. Off. |
| 9515319 | 6/1995 | WIPO |

OTHER PUBLICATIONS

Essien et al (1988), J. Med. Chem. vol. 31, pp. 898–901, "Synthesis of Diethylene Triamine Pentaacetic Acid Conjugated Inulin and Utility for Cellular Uptake of Liposomes".

Rongved et al (1991), Carbohydrate Research, vol. 214, pp. 325–330, "Cross linked, Degradable Starch Microspheres as Carriers of Paramagnetic Agents for Magnetic Resonance Imaging: Synthesis, Degradation, and Relaxation Properties".

Meares et al (1990), Br. J. Cancer, vol. 62, Suppl. X, pp. 21–26, "Macrocylic Chelates of Radiometals for Diagnosis and Therapy".

*Primary Examiner*—John Kight
*Assistant Examiner*—Dameron Jones
*Attorney, Agent, or Firm*—Bucknam and Archer

[57] ABSTRACT

New compounds endowed with a chelating property for paramagnetic bi- and trivalent metal ions, their chelates with said metal ions and their use as contrast agents in magnetic resonance imaging (MRI) are described. A method of obtaining images of organs and tissues of a human or animal body by means of nuclear magnetic resonance is also described.

11 Claims, No Drawings

PARAMAGNETIC CHELATES FOR NUCLEAR MAGNETIC RESONANCE DIAGNOSIS

This invention refers to new compounds endowed with a chelating property for paramagnetic bi- and trivalent metal ions, their chelates with said metal ions and their use as contrast agents in magnetic resonance imaging (MRI).

The use in medicine of a high number of these complexes is widely reported: for instance as stabilizers for the pharmaceutical preparations or antidotes in case of ingestion of toxic metal species.

Physiologically tolerable complexes formed by chelating agents and bi- or trivalent metal ions are used as diagnostic agents in imaging techniques such as X-ray, nuclear magnetic resonance (NMR) and scintigraphy.

In particular, magnetic resonance imaging (MRI) is a renowned powerful diagnostic procedure used in medical practice (see Stark, D. D., Bradley, W. G., Jr., Eds. "Magnetic Resonance Imaging" The C. V. Mosby Company, St. Louis, Mo. (USA), 1988) which relies on the use of paramagnetic pharmaceutical compositions, preferably containing chelated complexes of bi- or trivalent paramagnetic metal ions, usually belonging to the class of transition metals, or rare earth, with polyaminocarboxylic acids and/or their derivatives or analogues.

The images (basically coming from the NMR signal of water protons) are the result of a complex interaction of different parameters, such as proton density and $T_1$ and $T_2$ relaxation times. A contrast enhancement can be obtained through the administration of exogenous chemical substances which significantly change the resonance properties of nearby water protons (see Lauffer, R. B. Chem. Rev. 1987,87,901). Due to the high capacity of gadolinium complexes of reducing the relaxation times of hydrogen nuclei of nearby water molecules through dipolar interaction, scientists have investigated, patented and published a lot of works on these complexes. And some of them have been approved as MRI contrast media (Gd-DTPA/Dimeg, N-methylglucamine salt of gadolinium diethylenetriaminepentaacetic acid, MAGNEVIST®, Schering; Gd-DOTA/Dimeg, N-methylglucamine salt of gadolinium 1,4,7,10-tetraazacyclo dodecan-1,4,7,10-tetracetic acid, DOTAREM®, Guerbet).

A list of significant patent documents showing the state of the art in this diagnostic field, even though uncompleted, is represented by: EP 71564 (Schering), U.S. Pat. No. 4,639,365 (Sherry), U.S. Pat. No. 4,615,879 (Runge), DE-A-3401052 (Schering), EP 130934 (Schering), EP 65728 (Nycomed), EP 230893 (Bracco), U.S. Pat. No. 4,826,673 (Mallinckrodt), U.S. Pat. No. 4,639,365 (Sherry), EP 299795 (Nycomed), EP 258616 (Salutar), WO 8905802 (Bracco).

The choice of the suitable compound is based the evaluation of different parameters such as relaxivity, toxicity, distribution in the human body, excretion and so on. Three important properties are needed to use a complex of $Gd^{(3+)}$ as a potential MRI contrast agent. Firstly, a high thermodynamic stability (and possibly kinetic), that's to say a low tendency to release free $Gd^{(3+)}$ ions, highly toxic in vivo. Secondly, the presence of at least one water molecule directly coordinated to the metal in the inner coordination sphere and able to rapidly exchange with the bulk one. Thirdly, a high water solubility ($\geq 0.5$ mol/L). Although Gd-DTPA and Gd-DOTA are stable and water-soluble gadolinium chelates, they are ionic compounds (that's to say formally charged, in fact Gd-DTPA is equal to −2, while Gd-DOTA is −1) which are made neutral with the formation of N-methylglucamine salts. Therefore the solutions contain charged particles, which affect their osmolality characteristics. Injectable concentrated solutions (0.5–1.9M) of such salts are much more hyperesmoiai compared to blood and physiological fluids. Hyperosmoiality can produce, in vivo, oedemas and other undesired side effects.

As a consequence, several attempts have been made to develop new non-ionic metal complexes, which solve or limit the above mentioned drawbacks. A solution was proposed by Tweedle M. F. et al. in U.S. Pat. No. 4,885,363 which deals with the preparation of gadolinium complex with 10-(2-hydroxypropyl)-1,4,7,10-tetraazacyclododecan-1,4,7-triacetic acid (HP-DO3A, PROHANCE®, Squibb) in which one of the carboxylic groups has been removed to make the cadolinium complex neutral. Another way is represented by the conversion of one or more free carboxylic groups in the molecule of the complexing agent, into non-ionizable, neutral groups. For example, S. C. Quay, in patents U.S. Pat. Nos. 4,687,658 and 4,687,659 describes ester and amido derivatives of DTPA complexes (Gd-DTPA-bismethylamide, Gd-DTPA-BMA qadodiamide, OMNISCAN®, Salutar, was found particularly remarkable).

In the same way, Dean et al., in patent U.S. Pat. No. 4,826,673 describe mono- and polyhydroxyalkylamido DTPA derivatives and their use as complexing agents for paramagnetic ions. Patent applications DE 3324235 and DE 3324236 deal with mono- and polyhydroxyalkylamido DTPA derivatives and their use as complexing agents of paramagnetic ions. Even the Australian patent application 78995/87 claims amido complexing agents used for MRI and X-ray procedures.

Beyond these examples, patent application WO 92/04919 (Mallinckrodt) must also be cited, Zwitterionic complexes are claimed, but not disclosed, in which a negative and positive charge are simultaneously present in the complexing agent molecule, so that the metal complex results neutral. The negative charge is supplied by an anionic group selected from the group consisting of carboxylic, phosphonic, sulfonic, biphosphonic, phosphate and biphosphate groups. On the other hand, the positive charge is supplied by a cationic group selected from the group consisting of ammonium, phosphonium and sulfonium. The claimed products are not disclosed in the experimental section.

In conclusion, it can be stated that, even though plenty of work has been done in this field, the need of finding out new neutral or ionic complexes, which meet the above mentioned requirements, is still vivid.

This invention refers to compounds of general formula (I):

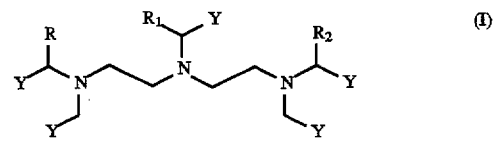

wherein

R, $R_1$, $R_2$, which are the same or different, are a hydrogen atom, with the proviso that at least one of them is different from hydrogen or are a —A—O—T residue in which:

A is —(CH$_2$)m—; —CH$_2$—C(CH$_3$)$_2$—, m is an integer between 1 and 5,

T has one of the following meanings:

a) is hydrogen, or, b) a straight or branched (C$_1$–C$_{10}$) alkyl group which can be substituted or not by 1–6 hydroxy and/or alkoxy groups, which can have or not one or more aldehyde, carboxy, or amino functions of formula —NR$_3$R$_4$, and which can also be a cyclic (C$_3$–C$_6$) residue interrupted or not by one or more N, O, S atoms, or, c) an arylalkyl group comprising 1–2 aryl residues, substituted or not, and 1–4 aliphatic carbon atoms, or, d) a phenyl group, substituted or not by one or more halo, hydroxyalkyl, hydroxy, alkoxy, carboxy, aldehyde, amino, mercapto, trifluoromethyl, amido, cyano, thiocyano, nitro, thioalkyl, sulfonic, sulfonic, phosphonic, phosphinic groups, or substituted by a straight or branched (C$_1$–C$_8$) alkyl, which is substituted or not by one or more hydroxy, alkoxy, carboxy, aldehyde, amino group, or, e) a polyoxaalkyl group comprising 1–10 oxygen atoms and 3–30 carbon atoms, wherein, R$_3$ and R$_4$ can be the same or different and represent:

a) hydrogen, or, b) a straight or branched (C$_1$–C$_{10}$) alkyl group, which can be substituted or not by 1–6 hydroxy and/or alkoxy group and/or by one or more aldehyde, carboxy, amino functions, wherein said amino substituent can be neutral, protonated or alkylated in order to supply a quaternary ammonium group, and which can also comprise a cyclic, aromatic or non-aromatic residue, which can contain or not N, C, S atoms, or, c) a polyoxaalkyl group comprising 1–10 oxygen atoms and 3–30 carbon atoms, which can have a terminal amino group, or d) R$_3$ and R$_4$, taken together, form a (C$_2$–C$_8$) chain interrupted or not by one or more N, O, S atoms, or, e) the —NR$_3$R$_4$ group can also represent a quanidine residue

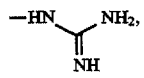

Y is a —COZ, or —PO(OH)Z or —POXZ or —SO$_2$Z or —SOZ group in which each residue Z independently represents a —OH or a —OR$_5$, or a —NR$_3$R$_4$ group wherein R$_3$ and R$_4$ are as previously defined, and R$_5$ is a straight or branched (C$_1$–C$_{10}$) alkyl which can be substituted or not by 1–6 hydroxy and/or alkoxy groups, X is an aliphatic, aromatic or heteroaromatic group, and with the proviso that some or all the acid and basic functions of said compounds of formula (I) can be both neutral and ionic.

This invention also include the preparation of the products of general formula (I) and their complexed salts, their uses and the relative pharmaceutical compositions for diagnostic use. These derivatives, if necessary, are salified with ions of organic or inorganic acids and bases and in some cases, chemically conjugated to suitable macromolecules or incapsulated in suitable carriers.

Particularly preferred compounds of this invention, are those represented by the following formulae (II) and (III),:

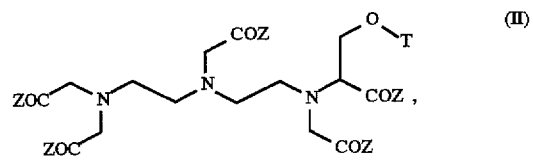

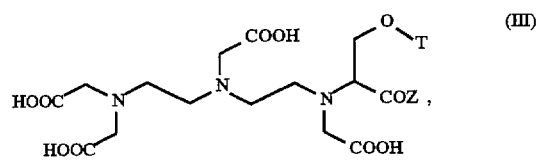

wherein T, and Z are as previously defined.

Particularly preferred are the compounds in which Z is equal to an amino group, —NR$_3$R$_4$, wherein R$_3$ and R$_4$ are as previously defined.

Non-limiting examples of these amino residues are —NH(CH$_2$)$_4$NHC(NH)NH$_2$, —NHCH(CH$_2$OH)$_2$, —NH(CH$_2$)$_2$O (CH$_2$)$_2$OH, —N(CH$_3$)(CH$_2$)$_3$N(CH$_3$)$_2$, —NH(CH$_2$)$_2$NH$_2$, —NHCH$_2$CH$_2$CHO, —NH(CH$_2$)$_3$N(CH$_3$)$_2$, —NHC(CH$_2$CH$_2$OH)$_3$,

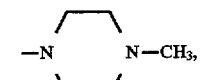

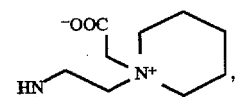

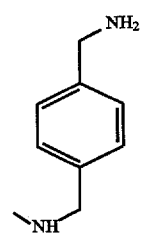

The new compounds of this invention show a good tolerability, which can make them particularly useful for the desired field of application.

The good water-solubility of the complexed compounds of this invention and the limited osmolality of the aqueous solutions of the same, are another remarkable quality which make them particularly suitable for their use in the above mentioned diagnostic procedures.

The chelates of this invention have shown interesting features regarding low osmolality. Available data referred to some of the preferred Gd-chelates of this invention are reported in EXAMPLE 10 of the experimental section, and compared to the known data of marketed products like MAGNEVIST® and OMNISCAN®.

The compounds of this invention have a wide range of applications, since they can be used for intravasal, (for instance i.v., intraarterial, intracoronaric, intraventricular administration and so on), intrathecal, intraperitoneal, intralymphatic, intracavital and intraparenchymal administration. Both soluble and less soluble compounds are suitable for oral or enteral administration, and therefore, specifically for the imaging of gastrointestinal (GI) tract. For parenteral administration they can be preferentially formulated as sterile aqueous solutions or suspensions, whose pH can range from 6.0 and 8.5.

These solutions or aqueous suspensions can be administered in concentrations ranging from 0.002M and 1.0M.

These formulation can be lyophilized and supplied as they are ready for the use. For the GI use or for injection to body cavities, these agents can be formulated as a solution or suspension containing suitable additives in order for example to control viscosity.

For oral administration they can be formulated according to preparation methods routinely used in the pharmaceutical technique or as coated formulations to gain extra protection from the acid pH of stomach, inhibiting the release of the chelated metal ion, which usually occurs at typical pH values of gastric juices.

Other excipients, such as for instance sweeteners and/or aromatizers can be equally added following known techniques of pharmaceutical formulations.

The solutions or suspensions of the compounds of this invention can also be formulated as aerosol to be used in aerosol-bronchography and instillation As far as diagnostic imaging is concerned, the chelates of this invention can also be used as contrast media in nuclear medicine. But in this case the metal ion which is chelated is a radioisotope, such as $^{51}Cr$, $^{68}Ga$, $^{111}In$, $^{99m}Tc$, $^{140}La$, $^{168}Yb$.

Metal ions suitable to form complexed salts with chelating agents of general formula (I) are bi- or trivalent ions of elements having atomic number selected 20 and 31, 39, 42, 43, 44, 49, or between 57 and 83; particularly preferred are $Fe^{(2+)}$, $Fe^{(3+)}$, $Cu^{(2+)}$, $Cr^{(3+)}$, $Gd^{(3+)}$, $Eu^{(3+)}$, $Dy^{(3+)}$, $La^{(3+)}$, $Yb^{(3+)}$ or $Mn^{(2+)}$.

Among preferred metal radioisotopes are in particular $^{51}Cr$, $^{68}Ga$, $^{111}In$, $^{99m}Tc$, $^{140}La$, $^{168}Yb$.

Preferred anions of inorganic acids which can be suitable for the salification of complexed chelates of this invention particularly comprise ions of the halohydric acids such as chlorides, bromides, iodides or other ions such as sulfates.

Preferred anions of organic acids suitable for this above mentioned aim comprise those of acids routinely used in pharmaceutical technique for the salification of basic substances such as acetate, succinate, citrate, fumarate, maleate.

Preferred cations of inorganic bases which can be suited to salify complexed chelates of this invention particularly comprise ions of alkaline or alkaline-earth metals such as potassium, sodium, calcium, magnesium and their mixtures.

Preferred cations of organic bases suitable for the a.m. aim, comprise, among others, those of primary, secondary and tertiary amines such as ethanolamine, diethanolamine, morpholine glucamine, N-methylglucamine, N,N-dimethylglucamine.

Preferred cations and anions of amino acids comprise, for instance, those of lysine, arginine or ornithine or of the aspartic acid glutamic acid.

Among macromolecules suitable for conjugation to complexed chelates of this invention the following molecules are included as non-limiting examples such as hormones (insulin), prostaglandines, steroidal hormones, aminosugars, peptides, proteins (albumine, human serum albumine), polylysine, lipids, antibodies such as monoclonal antibodies, polysaccharides.

The complexed chelates of this invention can be incapsulated in liposomes or they can be constituents of their chemical structure and used as uni- or multilamellar vesicles.

One the preferred method for preparing the chelating agents of general formula (I) and the complexed salts thereof, foresees the reaction of a derivative of the acid of formula (IV) (prepared according to patent EP-230893), in which T has the same meaning as previously defined,

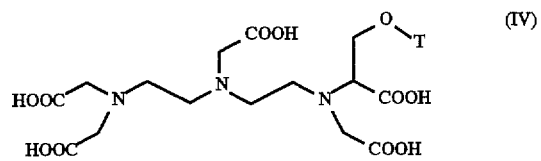

with $SOCl_2$ and a suitable alcohol $R_6OH$, in which $R_6$ is a ($C_1$–$C_5$) alkyl group, under a controlled temperature to selectively give a compound of formula (V).

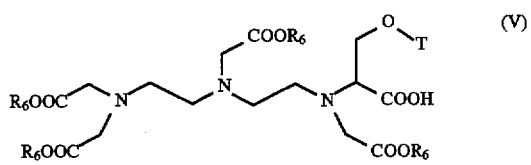

The successive reaction of compounds of formula (V) with the desired reagent, for instance, a secondary amine (VI), wherein $R_3$ and $R_4$ are as previously described,

leads to the product of formula (VII)

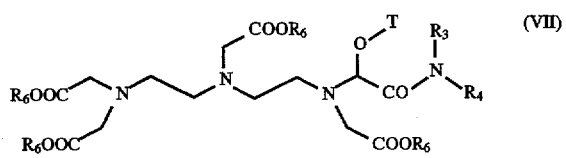

The reaction is activated by addition of diethoxyphosphoryl cyanide (DEPC) according to the synthesis of peptides (Shioiri,T et al., Tetrahedron, 32, 2211, 1976).

The successive conversion of ester groups into acid groups occurs in basic solution. The pH adjustment of the resulting solution to a suitable controlled value, allows the simultaneous formation of the complex with the desired metal by addition of the stoichiometric quantity of the oxide or a salt of the safe.

The reaction with DEPC preferably occurs in a dipolar aprotic solvent, such as dimethyl formamide (DMF) or dimethylacetamide (DMA), or in a mixture thereof at a temperature ranging from $-5°$ C. and $40°$ C., preferably between $0°$ C. and $25°$ C.

The hydrolysis of ester groups preferably occurs in the presence of a suitable organic or inorganic base such as sodium hydroxide, potassium hydroxide, potassium carbonate or, for example, tetrabutylammonium hydroxide (TBAOH) at a pH value between 8 and 12 and at a temperature ranging from $20°$ C. to $100°$ C., preferably from $20°$ C. to $70°$ C.

The formation of the metal-complex salt preferably occurs in water or in a suitable water-alcohol mixture, while the temperature ranges from $25°$ C. to $100°$ C., preferably from $40°$ C. to $80°$ C.

The choice of the metal ion and the possible neutralizing ion is strictly connected to the use of the complex to be produced.

As various changes could be made in the above compositions and methods without departing from the scope of the invention, it is intended that all matter contained in the description shall be interpreted as illustrative and not in a limiting sense.

COMPOUND 1 (EXAMPLE 1)

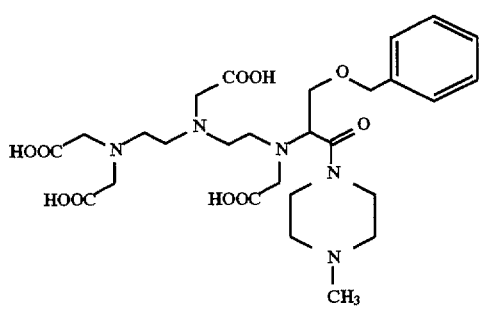

COMPOUND 2 (EXAMPLE 2)

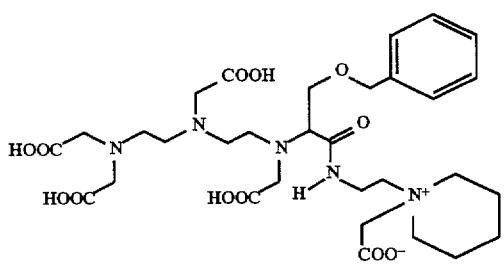

COMPOUND 3 (EXAMPLES 3 and 4)

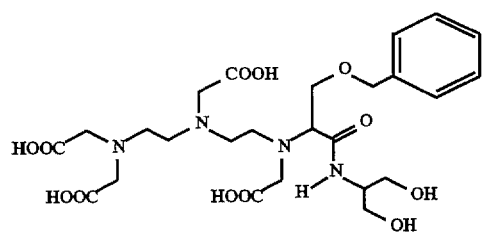

COMPOUND 4 (EXAMPLE 5)

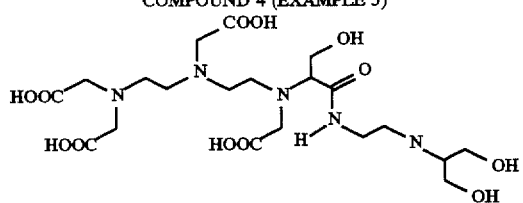

COMPOUND 5 (EXAMPLE 6)

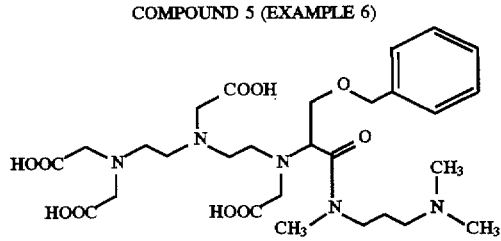

COMPOUND 6 (EXAMPLE 7)

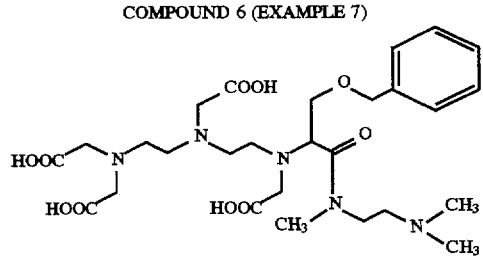

COMPOUND 7 (EXAMPLE 8)

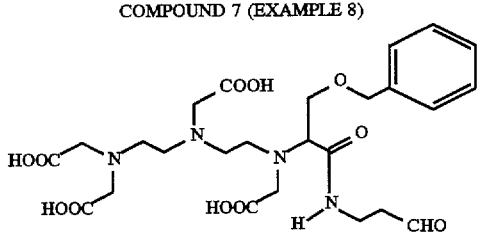

COMPOUND 8 (EXAMPLE 9)

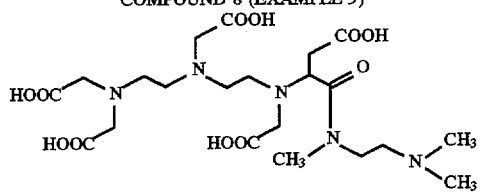

EXAMPLE 1

Gadolinium complex of 5,8,11-tris(carboxymethyl)-1-phenyl-4-(4-methyl-1-piperazinyl)carbonyl-2-oxa-5,8,11-triazatridecan-13-oic acid

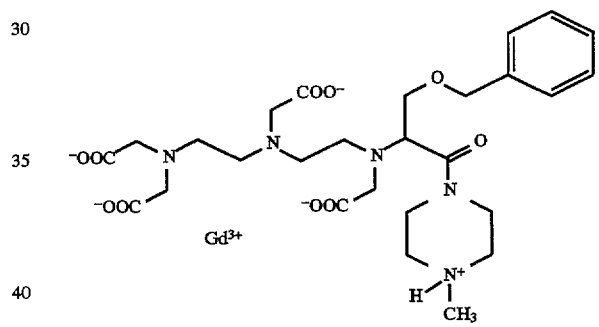

A) O-phenylmethyl-N-[2-methoxy-2-oxoethyl]-N-[2-[[2-[bis(2-methoxy-2-oxoethyl)amino]ethyl](2-methoxy-2-oxoethyl)amino]ethyl]-D,L-serine To a suspension of 40 g of 4-carboxy-5,8,11-tris(carboxymethyl)-1-phenyl-2-oxa-5,8,11-triazatridecan-13-oic acid (prepared according to patent EP-230893) (0.07789 mol) in 400 mL of anhydrous MeOH, kept at 0° C., 150 mL of thionyl chloride are added in 2 h. The clear solution heated at 25° C. is kept under magnetic stirring for 30 h. The solution is concentrated to dryness. To the resulting white solid, cooled with brine (−15° C.), 400 mL of Et$_2$O and, under slow stirring, 500 mL of a NaHCO$_3$ saturated solution (pH 10) are added. After separation, the aqueous phase, kept at 0° C., is acidified to pH 6.5 with 6N HCl and then extracted with EtOAc. The organic phase, dried on Na$_2$SO$_4$, is concentrated to dryness. 23.4 g of the desired product (0.0411 mol) are obtained.

Yield: 53%

HPLC: 98% (area %)

Stationary phase: E. Merck Lichrospher 100 RP-18 column; 5 μm; 250×4 mm

Mobile phase: Gradient elution;
A=aqueous solution of 0.01M $KH_2PO_4$ and 0.017M $H_3PO_4$
B=$CH_3CN$

| min | % A | % B |
| --- | --- | --- |
| 0 | 95 | 5 |
| 30 | 20 | 80 |
| 45 | 20 | 80 |

Flow: 1 mL min−1;
Temperature: 45° C.;
UV detector: 210 nm, 254 nm and 280 nm.
TLC: silica gel plate 60F 254 Merck
Eluent: $CH_2Cl_2$: MeOH=8:2 (v:v)
Detector: 0.5% KMNO4 in 0.1N NaOH Rf=0.5

$^1$H-NMR, $^{13}$C-NMR, IR and MS spectra are consistent with the assigned structure.

B) Methyl ester of 1-phenyl-4-(4-methyl-1-piperazinyl)carbonyl-5,8,11-tris(2-methoxy-2-oxoethyl)-2-oxa-5,8,11-triazatridecan-13-oic acid To a solution of 5.00 g of 1-methylpiperazine (5.56 mL; 49.92 mmol) and 11.30 g of compound A) (19.84 mmol) in 20 mL of DMF under inert atmosphere at 0°–5° C. 6.50 g of diethoxyphosphoryl cyanide (DEPC) (6.07 mL, 39.85 mmol) are added in 20 min. Then the solution is kept at room temperature with stirring for 1 h. The solution is diluted with 390 mL of a AcOEt : toluene=2:1 (v/v) mixture and washed with 0.001M HCl to remove the excess DEPC. The organic phase, is dried with $Na_2SO_4$ and concentrated to dryness under reduced pressure to give a yellow oil. The crude is purified by flash chromatography. Fractions with similar purity are collected and concentrated to dryness. 10.06 g of the desired product (15.43 mmol) are obtained.

Yield: 78%
HPLC: 97% (area %)
Stationary phase: E. Merck Lichrosorb RP-2 column; 5 mm; 250×4 mm
Mobile phase: Gradient elution;
A=aqueous solution of 0.01M $KH_2PO_4$ and 0.017M $H_3PO_4$
B=$CH_3CN$

| min | % A | % B |
| --- | --- | --- |
| 0 | 70 | 30 |
| 5 | 70 | 30 |
| 20 | 40 | 60 |
| 40 | 40 | 60 |

Flow: 1 mL min−1;
Temperature: 40° C.;
UV detector: 210 nm.
TLC: silica gel plate 60F 254 Merck
Eluent: $CHCl_3$: MeOH: 25% $NH_4OH$ (w/w)=9:1:0.05 (v/v/v)
Detector: 0.5% $KMNO_4$ in 0.1N NaOH Rf=0.5

$^1$H-NMR, $^{13}$C-NMR, IR and MS spectra are consistent with the assigned structure.

C) Gadolinium complex of 5,8,11-tris(carboxymethyl)-1-phenyl-4-(4-methyl-1-piperazinyl)carbonyl-2-oxa-5,8,11-triazatridecan-13-oic acid A solution of 9 g of compound B) (13.8 mol) in 140 mL of a $H_2O$/MeOH 6:1 (v/v) mixture is adjusted to pH 12 with 2N NaOH and kept at a constant pH with stirring for 18 h at 20° C. by addition of 27 mL of 2N NaOH. Methanol is distilled and the resulting aqueous solution pH is adjusted to 6.5 with 7.2 mL of 6N HCl and a solution of 5.13 g of $GdCl_3.6H_2O$ (13.8 mmol) in 25 mL of water is added. The solution is stirred for 30' and the pH is kept at pH 6.5 with 2N NaOH. The solution is desalted through nanofiltration, addition of HCl, and successive electrodialysis. The solution is concentrated to dryness to give 4.9 g of the desired product (6.53 mmol).

Yield: 47% m.p.: >200° C. (dec.)
K.F.: 6.26% (w/w)
HPLC: 100% (area %)
Stationary phase: E.Merck Lichrosorb RP-Select B column; 5 mm; 250×4 mm
Mobile phase: Gradient elution;
A=aqueous solution of 0.017M $H_3PO_4$
B=A:$CH_3CN$=3:7 (v/v)

| min | % A | % B |
| --- | --- | --- |
| 0 | 90 | 10 |
| 20 | 46.7 | 53.3 |

Flow: 1.5 mL min−1;
Temperature: 35° C.;
UV detector: 210 nm
Free metal: <0.1%
Elemental Analysis

|  | C | H | N | Gd |  |
| --- | --- | --- | --- | --- | --- |
| % calc.: | 43.25 | 5.11 | 9.34 | 20.97 |  |
| % found: | 40.58 | 5.94 | 8.66 | 19.34 | $H_2O$ 6.26 |

TLC: silica gel plate 60F 254 Merck
Eluent: 1-propanol: 25% NH OH (w/w)=7:3 (v/v)
Detector: 0.5% $KMNO_4$ in 0.1N NaCH Rf=0.4

IR and MS spectra are consistent with the assigned structure.

EXAMPLE 2

Gadolinium complex of 1-carboxymethyl-1-[13-carboxy-6,9,12-tris(carboxymethyl)-5-[(phenylmethoxy)methyl]-4-oxo-3,6,9,12-tetraazatridec-1-yl]piperidine hydroxide inner salt, salified with 1-desoxy-1-methylamino-D-glucitol (meglumine) (1:1)

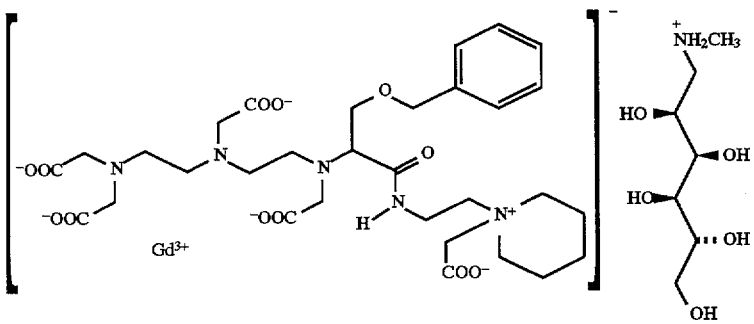

A) 2-Chloro-3-phenylmethoxy-N-[2-(1-piperidinyl)ethyl] propanamide 55.7 g of 1-(2-aminoethyl)piperidine (marketed product) (0.435 mol) and 125 mL of Et₃N (0.902 mol) are dissolved in 170 mL of CHCl₃. The mixture is cooled to 0° C., and a solution of 103.7 g of 2-chloro-3-(phenylmethoxy) propanoyl chloride (CAS RN 124628-32-6) (0.445 mol) in 250 mL of CHCl₃ is added dropwise (2.5 h) while the temperature is kept between 0° and 5° C. When the dropping is completed, the mixture is stirred at room temperature for 4 h. The reaction is followed through GC analysis. The reaction mixture is filtered, the solvent is evaporated under reduced pressure and the residue is diluted with Et₂O (1000 mL). The hydrochloride of the insoluble Et₃N, is filtered and the solution is washed with water (4×250 mL). The organic phase is removed, dried on Na₂SO₄ and evaporated under reduced pressure. The residue is dissolved in 80 mL of EtOH and 450 mL of MeCN and concentrated to dryness under reduced pressure. The process is repeated twice. The crude is dissolved in 500 mL of MeCN, evaporated under reduced pressure and dried. 137.2 g of the desired product (0.405 mol) are obtained.

Yield: 93%
Elemental Analysis

|  | C | H | N | Cl |  |
|---|---|---|---|---|---|
| % calc.: | 62.85 | 7.76 | 8.62 | 10.91 |  |
| % found: | 62.70 | 7.80 | 8.50 | 10.70 | H₂O 0.53 |

¹H-NMR, ¹³C-NMR, IR and MS spectra are consistent with the assigned structure.

B) 2-[[2-[(2-Aminoethyl)amino]ethyl]amino]-3-(phenylmethoxy)-N-[2-(1-piperidinyl)ethyl]propanamide 136.0 g of compound A) (0.402 mol) and 225 mL of diethylenetriamine (marketed product) (2.07 mol) are dissolved in 500 mL of MeCN and the solution is heated at 50° C. and stirred for 72 h. After checking by GC analysis that the starting amine has vanished, the mixture is cooled to room temperature, the precipitated diethylenetriamine hydrochloride is filtered, and the solution is concentrated to dryness under reduced pressure. The exceeding diethylenetriamine is distilled off under vacuum and the residue is purified by flash chromatography. 89.7 g of the desired product (0.21 mol) are obtained.

Yield: 53%
AgNO₃, 0.1N: 3.4%
TLC: silica gel plate 60F 254 Merck
Eluent: CH₂Cl₂:MeOH:25% NH₄OH (w/w)=20:10:1 (v/v/v)
Detector: 0.5% KMnO₄ in 0.1N NaOH Rf=0.65

¹H-NMR, ¹³C-NMR, IR and MS spectra are consistent with the assigned structure.

C) 1-Carboxymethyl-1-[13-carboxy-6,9,12-tris (carboxymethyl)-5-[(phenylmethoxy)methyl]-4-oxo-3,6,9,12-tetraazatridec-1-yl]piperidine hydroxide inner salt A solution of 50 mL of t-butyl bromoacetate (0.310 mol) in 35 mL of 1,2-dichloroethane is added dropwise to a solution of 36.5 g of compound B) (70 mmol) and 110 mL of diisopropylethylamine (0.647 mol) in 50 mL of 1,2-dichloroethane while the temperature of the reaction mixture is kept at 0° C. When the addition is completed, the mixture is stirred at room temperature for 72 h. The solvent is evaporated under reduced pressure; the residue is dissolved in 500 mL of AcOEt and washed with H₂O. The organic phase is separated, dried on Na₂SO₄ and concentrated to dryness under reduced pressure to give an orange oil. The oil is dissolved in 500 mL of CH₂Cl₂, the solution is cooled to 0° C. and 250 mL of CF₃COOH are added dropwise (1 h). The reaction mixture is stirred at room temperature for 72 h, the solvent is evaporated under reduced pressure and the residue, dissolved in CH₂Cl₂, is re-evaporated to remove CF₃COOH. The resulting residue (as trifluoroacetate) is dissolved in 250 mL of CH₂Cl₂ and extracted with 500 mL of 1N HCl to give hydrochloride. The aqueous phase, washed with CH₂Cl₂, is concentrated to dryness. The solid is dissolved in 1N HCl and concentrated to dryness to give a crude which is purified by reverse-phase chromatography on Lobar® RP-18 column. 4.5 g of the desired product (0.0066 mol) are obtained.

Yield: 9.4% m.p.: 126°–128° C. (dec.)
K.F.: 5.86% (w/w)
HPLC: 95% (area %)
Stationary phase: E. Merck Lichrosorb RP-Select B column; 5 mm; 250×4 mm;
Mobile phase: Isocratic elution: A/B=83:17:
A=aqueous solution of 0.01M KH₂PO₄ and 0.017M H₃PO₄
B=CH₃OH
Flow: 1 mL min−1;
Temperature: 45° C.;
UV detector: 210 nm.
Elemental Analysis

|  | C | H | N | Cl |  |
|---|---|---|---|---|---|
| % calc.: | 54.12 | 6.95 | 10.27 |  |  |
| % found: | 51.54 | 7.08 | 9.57 | <0.1 | H₂O 5.86 |

¹H-NMR, ¹³C-NMR, IR and MS spectra are consistent with the assigned structure.

D) Gadolinium complex of 1-carboxymethyl-1-[13-carboxy-6,9,12-tris (carboxymethyl)-5-[(phenylmethoxy)methyl]-4-oxo-3,6,9,12-to tetraazatridec-1-yl]piperidine-hydroxide inner salt, salified with 1-desoxy-1-methylamino-D-glucitol (meglumine) (1:1)

To a solution of 3.0 g of compound C) (4.4 mmol) in H$_2$O, at room temperature, a solution of 1.64 g of GdCl$_3$.6 H$_2$O (4.4 mmol) in 20 mL H$_2$O is added and the solution pH is adjusted to 6.5 by addition of 17 mL of meglumine 1N. The solution is stirred for 48 h. After complexometric analysis, for detection of free metals, additional ligand is added (30 mg; 0.04 mmol) and kept reacting for 2 h. when the reaction is completed, the exceeding meglumine hydrochloride is removed through electrodialysis from the solution containing the product. The retentate is concentrated to dryness to give 2.1 g of the desired product (2 mmol).

Yield: 46% m.p.: ⁻200° C. (dec.)

K.F.: 3.75% (w/w)

HPLC: 98.5% (area %)

Stationary phase: E. Merck Lichrosorb RP-2 column; 5 mm; 250×4 mm

Mobile phase: Gradient elution;

A=aqueous solution of 0.01M KH$_2$PO$_4$ and 0.017M H$_3$PO$_4$

B=CH$_3$CN

| min | % A | % B |
|---|---|---|
| 0 | 70 | 30 |
| 5 | 70 | 30 |
| 20 | 40 | 60 |
| 40 | 40 | 60 |

Flow: 1 mL min−1;
Temperature: 40° C.;
UV detector: 210 nm.
Elemental Analysis

| | C | H | N | Gd | |
|---|---|---|---|---|---|
| % calc.: | 44.26 | 5.96 | 8.15 | 15.25 | |
| % found: | 43.26 | 6.44 | 7.71 | 14.79 | H$_2$O 3.75 |

TLC: silica gel plate 60F 254 Merck
Eluent: 1-propanol: 25% NH$_4$OH (w/w)=7:3 (v/v)
Detector: 0.5% KMNO$_4$ in 0.1N NaOH Rf=0.3

IR and MS spectra are consistent with the assigned structure.

EXAMPLE 3

Gadolinium complex with (4R,S)-5,8,11-tris (carboxymethyl)-1-phenyl-4-[[[2-hydroxy-1-(hydroxyethyl)ethyl]amino]carbonyl]-2-oxa-5,8,11-triazatriecan-13-oic acid, salified with 1-desoxy-1-(methylamino)-D-glucitol (1:1)

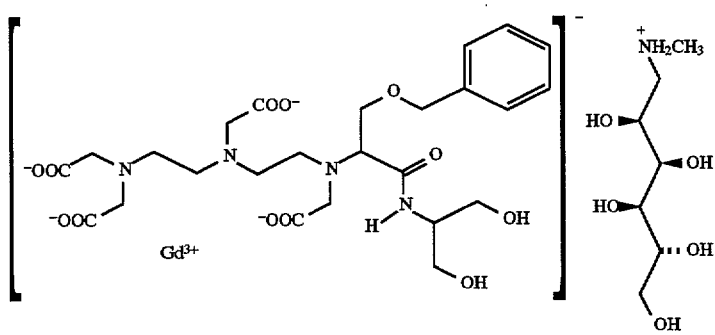

A) 2-chloro-3-phenylmethoxy-N-[2-hydroxy-1-(hydroxyethyl)ethyl]propanamide

To a solution of 32.6 g of 2-amino-1,3-propanediol (serinol, marketed product) (0.36 mol) in 150 mL of water and 250 mL of THF, a solution of 70 g of 2-chloro-3-(phenylmethoxy)propionyl chloride (0.3 mol) in 150 mL of THF is added dropwise, for 2 h by cooling it with water (18° C.). The solution pH is 12 at the beginning, then drops for the addition of the acid chloride to 10 and this value is kept by addition of 46.2 mL of 6N NaOH (0.28 mol). When the reaction is completed (pH=10 constant), the solution is diluted with water and concentrated to cause the precipitation of a white solid which is filtered and washed with water. Through water crystallization 62.2 g of the desired product (0.216 mol) are obtained.

Yield: 72% m.p.: 133°–134° C. (dec.)

Elemental Analysis

| | C | H | Cl | N | |
|---|---|---|---|---|---|
| % calc.: | 54.27 | 6.30 | 13.32 | 4.87 | |
| % found: | 54.19 | 6.38 | 12.24 | 4.84 | H$_2$O 0.22 |

$^1$H-NMR, $^{13}$C-NMR, IR and MS spectra are consistent with the assigned structure.

B) 2-[[2-[(2-aminoethyl)amino]ethyl]amino]-3-(phenylmethoxy)-N-[2-hydroxy-1-(hydroxymethyl)ethyl] propanamide 190 mL of diethylenetriamine (1.75 mol) are added to a suspension of 100 g of compound A) (0.35 mol) in 500 mL of MeCN and the resulting solution is heated at 50° C. with stirring for 48 h. After checking through HPLC that chloroamide has been totally removed, the solvent is evaporated under reduced pressure, the diethylenetriamine in excess is distilled off under vacuum, the residue is purified by silica gel chromatography. The fractions containing the product are collected, concentrated to dryness. The residue is purified by flash chromatography. Fractions with similar purity are concentrated to dryness to give 76.7 g of the desired product (0.192 mol).

Yield: 57%

Elemental Analysis

|  | C | H | N |
|---|---|---|---|
| % calc.: | 57.60 | 8.53 | 15.81 |
| % found: | 55.21 | 8.35 | 14.72 |

TLC: silica gel plate 60F 254 Merck
Eluent: $CH_2Cl_2$:MeOH:25% NH OH=10:4:1 (v/v/v)
Detector: 0.5% $KMnO_4$ in 0.1N NaOH Rf=0.33
$^1$H-NMR, $^{13}$C-NMR, IR and MS spectra are consistent with the assigned structure.

C) (4R,S)-5,8,11-tris(carboxymethyl)-1-phenyl-4-[[[2-hydroxy-1-(hydroxymethyl)ethyl]amino]carbonyl]-2-oxa- 5,8,11-triazatridecan-13-oic acid tetra(1,1-dimethylethyl)ester A solution of 200 mL of t-butyl bromoacetate (1.24 mol) in 200 mL of 1,2-dichloroethane is added to a suspension of 78.0 g of compound B) (0.21 mol) and 400 mL of diisopropylethylamine (2.35 mol) in 500 mL of 1,2-dichloroethane while the temperature is kept around 29° C. The mixture is kept at room temperature with stirring for 96 h, and the reaction is checked by HPLC analysis. The resulting white solid is filtered, the solvent evaporated under reduced pressure, the residue dissolved in AcOEt and evaporated. The residue is theft re-dissolved in 250 mL of AcOEt and filtered, diluted with AcOEt and washed with 500 mL of $H_2O$, 500 mL of NaOH 0.2M and 500 mL of $H_2O$. The organic phase is separated, dried on $Na_2SO_4$, and concentrated to dryness to give a yellow oil which is dissolved in AcOEt and purified by flash chromatography. 76.0 g of the desired product (0.081 mol) are obtained.
Yield: 39%
Elemental Analysis

|  | C | H | N |
|---|---|---|---|
| % calc.: | 60.72 | 8.70 | 6.91 |
| % found: | 60.38 | 8.72 | 6.60 |

TLC: silica gel plate 60F 254 Merck
Eluent: $CH_2Cl_2$: $CH_3OH$=9:1 (v/v)
Detector: 0.5% $KMnO_4$ in 0.1N NaOH Rf=0.57
$^1$H-NMR, $^{13}$C-NMR, IR and MS spectra are consistent with the assigned structure.

D) (4R,S)-5,8,11-tris(carboxymethyl)-1-phenyl-4-[[[2-hydroxy-1-(hydroxymethyl)ethyl]amino]carbonyl]-2-oxa-5,8,11-triazatridecan-13-oic acid 57 g of compound C) (0.063 mol) are dissolved in 500 mL of $CH_2Cl_2$. To the solution, cooled to 0° C., 250 mL of $CF_3COOH$ are added dropwise and the solution is kept at room temperature for 72 h. After evaporation under reduced pressure, the residue is dissolved in $CH_2Cl_2$ and evaporated. The process is repeated several times. The residue is then dissolved in 800 mL of $CH_2Cl_2$ and extracted with 800 mL of $H_2O$. The aqueous phase is separated, reduced to a quarter of the volume under reduced pressure, diluted with 209 mL of 1N HCl and concentrated to dryness while the temperature is kept at −30° C. The solid is diluted with 200 mL of 1N HCl and concentrated to dryness. Then the solid is diluted with 200 mL of $H_2O$, concentrated to dryness, diluted with $H_2O$ and purified by reverse-phase silica gel chromatography on Lobar® RP-18 column. Fractions with similar purity are collected, the solution is concentrated under reduced pressure and then lyophilized. 20.82 g of the desired product (0.034 mol) are obtained.

Yield: 55%
0.1N $ZnSO_4$: 98.3% (w/w)
0.1N NaOH: 97.7% (w/w)
Elemental Analysis

|  | C | H | N |  |
|---|---|---|---|---|
| % calc.: | 51.18 | 6.53 | 9.55 |  |
| % found: | 50.53 | 6.65 | 9.29 | $H_2O$ 1.57 |

TLC: silica gel plate RP-18 F254 Merck
Eluent: $H_2O$:MeCN=10:90 (v/v) containing 1% of 85% $H_3PO_4$
Detector: 0.5% $KMnO_4$ in 0.1N NaOH Rf=0.37
$^1$H-NMR, $^{13}$C-NMR, IR and MS spectra are consistent with the assigned structure.

E) Gadolinium complex (4R,S)-5,8,11-tris(carboxymethyl)-1-phenyl-4-[[[2-hydroxy-1-(hydroxymethyl)ethyl]amino]carbonyl]-2-oxa-5,8,11- triazatridecan-13-oic acid, salified with 1-desoxy-1-(methylamino)-D-glucitol (1:1)

11.18 g of compound C) (18.68 mmol) and 3.72 g of 1-desoxy-1-(methylamino)-D-glucitol (18.76 mmol) are dissolved in 200 mL of $H_2O$ and 3.41 g of $Gd_2O_3$ (9.41 mmol) are added to the solution. The reaction mixture is kept with stirring at room temperature for 48 h, and then filtered and lyophilized. 17.65 g of the desired product (18.09 mol) are obtained.
Yield: 97% m.p.: 188° C.
EDTA 0.001M: <0.15% (w/w)
Elemental Analysis

|  | C | H | N | Gd |  |
|---|---|---|---|---|---|
| % calc.: | 41.06 | 5.60 | 7.48 | 16.80 |  |
| % found: | 39.74 | 5.73 | 7.22 | 16.04 | $H_2O$ 4.14 |

TLC: silica gel plate RP-18 F254 Merck
Eluent: phosphate buffer pH 7: MeCN-90:10 (v/v)
Detector: 1% $KMnO_4$ in 1N NaOH Rf=0.57
IR and MS spectra are consistent with the assigned structure.

EXAMPLE 4

Gadolinium complex with non-salified (4R,S)-5,8,11-tris(carboxymethyl)-1-phenyl-4-[[[2-hydroxy-1-(hydroxymethyl)ethyl]amino]carbonyl]-2-oxa-5,8,11-triazatridecan-13-oic acid

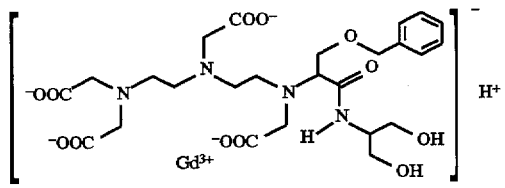

0.506 g of (4R,S)-5,8,11-tris(carboxymethyl)-1-phenyl-4-[[[2-hydroxy-1-(hydroxymethyl)ethyl]amino]carbonyl]-2-oxa-5,8,11-triazatridecan-13-oic acid (prepared according to EXAMPLE 3) (0.846 mmol) are dissolved in 10 mL of $H_2O$ and 0.158 g of $Gd_2O_3$ (0.437 mmol) are added to the solution. The resulting suspension is kept with stirring at room temperature for 48 h obtaining the solubilization of the precipitate. After filtration, evaporation under reduced pressure and drying 0.584 g of the desired product (0.709 mmol) are obtained.

Yield: 84% m.p.: 225° C. (dec.)

EDTA 0.001M: 0.6% (w/w)

Elemental Analysis

|  | C | H | N | Gd |  |
|---|---|---|---|---|---|
| % calc.: | 40.53 | 4.76 | 7.56 | 21.23 |  |
| % found: | 36.74 | 5.31 | 6.85 | 19.15 | $H_2O$ 9.90 |

IR and MS spectra are consistent with the assigned structure.

EXAMPLE 5

Gadolinium complex of 3,6,9-tris(carboxymethyl)-14-hydroxy-10,13-bis(hydroxymethyl)-11-oxo-3,6,9,12-tetraazatetradecanoic acid, salified with 17desoxy-1-(methylamino)-D-glucitol (1:1)

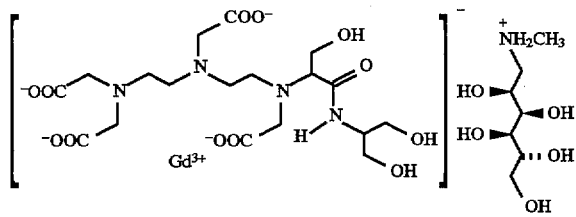

0.65 g of gadolinium complex with (4R,S)-5,8,11-tris(carboxymethyl)-1-phenyl-4-[[[2-hydroxy-1-(hydroxymethyl)ethyl]amino]carbonyl]-2-oxa-5,8,11-triazatridecan-13-oic acid salt of 1-desoxy-1-(methylamino)-D-glucitol (1:1) (prepared according to EXAMPLE 3) (0.68 mmol) are dissolved in. 25 mL of water. 1.13 g of 10% Pd/C suspended in 25 mL of water are added to the solution and the mixture is hydrogenated at room temperature and atmospheric pressure. After 3 h, the reaction mixture is filtered. After evaporation under reduced pressure and drying of the mixture, 0.48 g of the desired product (0.51 mmol) are obtained.

Yield: 76% m.p.: 158° C. (dec.)

K.F.: 9.47% (w/w)

$GdCl_3$ 0.001M: 0.7% (w/w)

Elemental Analysis

|  | C | H | N | Gd |  |
|---|---|---|---|---|---|
| % calc.: | 35.49 | 5.48 | 8.28 | 18.59 |  |
| % found: | 32.09 | 5.84 | 7.46 | 16.80 | $H_2O$ 9.47 |

IR and MS spectra are consistent with the assigned structure.

EXAMPLE 6

Gadolinium complex of 9,12,15-tris(carboxymethyl)-2,6-dimethyl-7-oxo-8-[(phenylmethoxy)methyl]-2,6,9,12,15-pentaazaeptadecan-17-oic acid inner salt

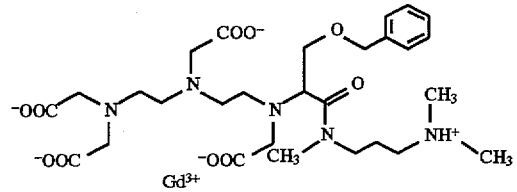

A) 9,12,15-tris(2-methoxy-2-oxoethyl)-2,6-dimethyl-7-oxo-8-[(phenylmethoxy)methyl]-2,6,9,12,15-pentaazaeptadecan-17-oic acid methyl ester To a solution of 7.76 g of N,N,N'-trimethyl-1,3-propanediamine (marketed product) (66.77 mmol) and 15.21 g of O-phenylmethyl-N-(2-methoxy-2-oxoethyl)-N-[2-[[2-[bis(2-methoxy-2-oxoethyl)amino]ethyl](2-methoxy-2-oxyethyl)amino]ethyl]-D,L-serine (prepared according to EXAMPLE 1) (26.70 mmol) in 60 mL of DMF under inert atmosphere and at 0° C., 8.7 g of DEPC (marketed product) (53.40 mmol) are added for 30 min. The solution is stirred far 1 h at 0° C. then kept at room temperature and diluted with 300 mL of a AcOEt: toluene=2:1 (v/v) mixture. The solution is washed, to remove the remaining DEPC, with 0.001M HCl. The organic phase, dried with $Na_2SO_4$, is evaporated under reduced pressure up to a constant weight. The residue is purified by flash chromatography. Fractions with a similar purity are collected and concentrated to dryness. 10.8 g of the desired product (16.17 mmol) are obtained.

Yield: 61%

HPLC: 100% (area %)

Stationary phase: E. Merck Lichrosorb RP-Select B column; 5 mm; 250×4 mm

Mobile phase: Gradient elution;

A=aqueous solution of 0.017M $H_3PO_4$

B=A/$CH_3CN$=3:7 (v/v)

| min | % A | % B |
|---|---|---|
| 0 | 90 | 10 |
| 20 | 46.7 | 53.3 |

Flow: 1.5 mL min–1;

Temperature: 35° C.;

UV detector: 210 nm.

TLC: silica gel plate 60F 254 Merck

Eluent: $CHCl_3$:$CH_3OH$=9:1 (v/v)

Detector: 0.5% $KMNO_4$ in 0.1N NaOH Rf=9.4

$^1$H-NMR, $^{13}$C-NMR, IR and MS spectra are consistent with the assigned structure.

B) Gadolinium complex of 9,12,15-tris(carboxymethyl)-2,6-dimethyl-7-oxo-8-[(phenylmethoxy)methyl]-2,6,9,12,15-pentaazaeptadecan-17-oic acid inner salt A solution of 6.0 g of compound A) (8.98 mmol) in 60 mL of a $H_2O$ $CH_3OH$ 6:1 (v/v) mixture is adjusted to pH 12 with 2N NaOH and kept at a constant pH with stirring for 18 h at 20° C. by controlled addition of 35 mL of 1N NaOH. After methanol distillation, the aqueous solution pH is adjusted to 6.5 with 4.7 mL of 6N HCl and a solution of 3.34 g of $GdCl_3·6H_2O$ (8.98 mmol) in 25 mL of water is added. The solution is stirred for 30 min, while the pH is kept at 6.5 with 1N NaOH. The solution is desalted through electrodialysis and concentrated to dryness. The product is purified by reverse-phase chromatography on Lobar® RP-18 column. Fractions with similar purity are collected and concentrated under reduced pressure. 4.0 g of the desired product (5.22 mmol) are obtained.

Yield: 58% m.p.: >200° C. (dec.)
K.F.: 5.51% (w/w)
HPLC: 100% (area %)
Stationary phase: E.Merck Lichrosorb RP-Select B column; 5 mm; 250×4 mm
Mobile phase: Gradient elution;
A=aqueous solution of 0.017M $H_3PO_4$
B=A/$CH_3CN$=3:7

| min | % A | % B |
|---|---|---|
| 0 | 90 | 10 |
| 20 | 46.7 | 53.3 |

Flow: 1.5 mL min−1;
Temperature: 35° C.;
UV detector: 210 nm.
Elemental Analysis

|  | C | H | N | Gd |  |  |
|---|---|---|---|---|---|---|
| % calc.: | 43.91 | 5.53 | 9.14 | 20.53 |  |  |
| % found: | 41.39 | 6.13 | 8.59 | 20.41 | $H_2O$ | 5.51 |

TLC: silica gel plate 60F 254 Merck
Eluent: 1-propanol/25% $NH_4OH$ (w/w)=7:3 (v/v)
Detector: 0.5% $KMnO_4$ in 0.1N NaOH Rf=0.4
IR and MS spectra are consistent with the assigned structure.

In the same way the $Mn^{2+}$ complex of 9,12,15-tris(carboxymethyl)-2,6-dimethyl-7-oxo-8-[(phenylmethoxy)methyl]-2,6,9,12,15-pentaazaeptadecan-17-oic acid salt of 1-desoxy-1-(methylamino)-D-glucitol (1:2) is prepared.

EXAMPLE 7

Gadolinium complex of 8,11,14-tris(carboxymethyl)-2,5-dimethyl-6-oxo-7-[(phenylmethoxy)methyl]-2,5,8,11,14-pentaazahexadecan-16-oic acid inner salt

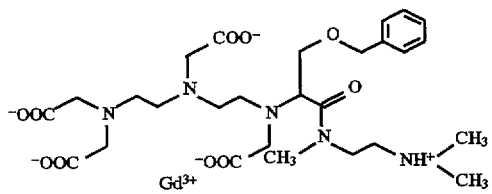

A) 8,11,14-tris(carboxymethyl)-2,5-dimethyl-6-oxo-7-[(phenylmethoxy) methyl]-2,5,8,11,14-pentaazahexadecan-16-oic acid methyl ester Following the procedure described in EXAMPLE 1, to a solution of 18.93 g of N,N,N'-trimethylethylenediamine (184 mmol) and 42 g of O-phenylmethyl-N-(2-methoxy-2-oxoethyl)-N-[2-[[2-[bis(2-methoxy-2-oxoethyl)amino]ethyl](2-methoxy-2-oxoethyl)amino]ethyl]-D,L-serine (73.7 mmol) in 80 mL of DMF under inert atmosphere and at 0° C. 20.9 g of DEPC (147 mmol) are added in 30 min. 30 g of the desired product (45.88 mmol) are obtained.
Yield: 62.2%

HPLC: 99.3% (area %)
Stationary phase: E.Merck Lichrospher 100 RP-18 column; 5 mm; 250×4 mm
Mobile phase: Gradient elution;
A=aqueous solution of 0.01M $KH_2PO_4$ and 0.017M $H_3PO_4$
B=$CH_3CN$

| min | % A | % B |
|---|---|---|
| 0 | 95 | 5 |
| 30 | 20 | 80 |
| 45 | 20 | 80 |

Flow: 1 mL min−1;
Temperature: 45° C.;
UV detector: 210 nm, 254 nm e 280 nm.
TLC: silica gel plate 60F 254 Merck
Eluent: $CHCl_3$:$CH_3OH$=9:1 (v/v)
Detector: 0.5% $KMnO_4$ in 0.1N NaOH Rf=0.5
$^1$H-NMR, $^{13}$C-NMR, IR and MS spectra are consistent with the assigned structure.

B) 8,11,14-tris(carboxymethyl)-2,5-dimethyl-6-oxo-7-[(phenylmethoxy)methyl]-2,5,8,11,14-pentaazahexadecan-16-oic acid Following the procedure of EXAMPLE 1, 6 g of compound A) (9.18 mmol) are treated with 40 mL of a $H_2O$/MeOH 1:1 (v/v) mixture and the solution pH is adjusted to 12 by addition of 18 mL of 2N NaOH. The solution is kept at pH 12, then acidified to pH 3 with HCl 3N. After purifying the solution through electrodialysis, 3.0 g of the desired product (5.02 mmol) are obtained.
Yield: 54.7%
Elemental Analysis

|  | C | H | N |
|---|---|---|---|
| % calc.: | 54.24 | 7.26 | 11.72 |
| % found: | 53.04 | 7.76 | 11.38 |

$^1$H-NMR, $^{13}$C-NMR, IR and MS spectra are consistent with the assigned structure.

C) Gadolinium complex of 8,11,14-tris(carboxymethyl)-2,5-dimethyl-6-oxo-7-[(phenylmethoxy)methyl]-2,5,8,11,14-pentaazahexadecan-17-oic acid inner salt A solution of 23 g of compound B) (38.48 mmol) in 200 mL of $H_2O$ is taken to pH 6.5 with 6N HCl and a solution of 14.3 g of $GdCl_3 \cdot 6H_2O$ (38.48 mmol) in 75 mL of water is added. The solution is stirred for 30 min by keeping the pH at 6.5 with 6N NaOH. The solution is desalted through HPLC. Fractions are collected and concentrated under reduced pressure. 4.0 g of the desired product (5.22 mmol) are obtained.
Yield: 90% m.p.: >200° C. (dec.)
K.F.: 7.68% (w/w)
HPLC: 100% (area %)
Elemental Analysis

|  | C | H | N | Gd |  |  |
|---|---|---|---|---|---|---|
| % calc.: | 43.13 | 5.36 | 9.31 | 20.91 |  |  |
| % found: | 39.82 | 6.18 | 8.61 | 20.71 | $H_2O$ | 7.68 |

IR and MS spectra are consistent with the assigned structure.

EXAMPLE 8

5,8,11-tris(carboxymethyl)-1-phenyl-4-[(3-oxypropyl)amino]carbonyl-2-oxa-5,8,11-triazatridecan-13-oic acid

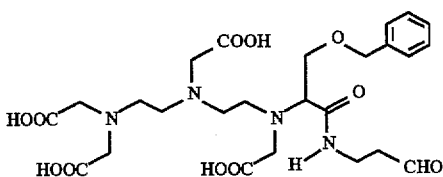

A) 2-(2-Aminoethyl)-1,3-dioxalone

A suspension of 50 g of 2-(2-bromoethyl)-1,3-dioxalone (CAS RN 5754-35-8) (0.27 mL, 32.5 mol), 62.5 g of phthalimide potassium (0.34 mol), 9.16 g of $Bu_4N^+HSO_4^-$ (0.027 mol) in 150 mL of toluene is heated at 100° C. and under $N_2$ for 3 h. After cooling to room temperature, the mixture is filtered and concentrated to dryness. By residue crystallization from abs. EtOH the phthalimide derivative is given. A solution of 58.5 g of $NH_2NH_2.H_2O$ (1.17 mL; 56.8 mol), 64.36 g of phthalimido derivative (0.26 mol) in 2 L of abs EtOH is heated under $N_2$ for 2.5 h. After cooling at 0° C., the precipitated phthahidrazide is filtered out. After concentration to dryness of the filtrate 23.26 g of the desired product (0.198 mol) are obtained.

Yield: 73%

Elemental Analysis

|  | C | H | N |
|---|---|---|---|
| % calc.: | 51.25 | 9.48 | 11.94 |
| % found: | 49.27 | 9.77 | 10.53 |

$^1$H-NMR, $^{13}$C-NMR, IR and MS spectra are consistent with the assigned structure.

B) 2-Chloro-N-[2-(1,3-dioxolan-2-yl)ethyl]-3-(phenylmethoxy)propanamide

A solution of 69.63 g of 2-chloro-3-(phenylmethoxy)propanoyl chloride (0.299 mol) in 90 mL of $CHCl_3$ is added to a solution of 35.49 g of compound A) (0.303 mol) and of 60.3 g of triethylamine (83 mL; 0.596 mol) in 100 mL of $CHCl_3$ under inert atmosphere, while the temperature is kept at 0°–5° C. The reaction mixture is stirred for 5 h at 25° C., then is washed with water. The organic phase is dried with $Na_2SO_4$ and concentrated to dryness to give a clear oil, which is purified by flash chromatography. Fractions with similar purity are collected and concentrated to dryness. 61.68 g of the desired product (0.197 mol) are obtained.

Yield: 66%

TLC: silica gel plate 60F 254 Merck

Eluent: AcOEt: n-hexane=1:1 (v/v)

Detector: 0.5% $KMnO_4$ in 0.1N NaOH Rf=0.34

$^1$H-NMR, $^{13}$C-NMR, IR and MS spectra are consistent with the assigned structure.

C) 5,8,11-tris[2-(1,1-dimethylethoxy)-2-oxoethyl]-1-phenyl-4-[[2-(1,3-dioxolan-2-yl)ethyl]amino]carbonyl-2-oxa-5,8,11-triazatridecan-13-oic acid (1,1-dimethylethyl) ester 30.97 g of diethylenetriamine (0.300 mol) are added to a solution of 20.94 g of compound B) (0.067 mol) in 100 mL of MeCN under inert atmosphere. The mixture is kept at 50° C. for 72 h and at 80° C. for 8 h. After cooling at 0° C., the precipitate (diethylenetriamine hydrochloride) is filtered and washed with 50 mL of MeCN. After evaporating the solvent under reduced pressure, the exceeding diethylenetriamine is removed through distillation under vacuum. The crude is dissolved in 80 mL of AcOEt, filtered (the last traces of diethylenetriamine hydrochloride are removed) and concentrated to dryness to give a brownish oil, which is purified by silica gel chromatography [eluent $CHCl_3$/MeOH/25% $NH_4OH$ (w/w) 20: 4:0.4 (v/v/v)]. Fractions with similar purity are collected and concentrated to dryness to give 2-[[2-[(2-aminoethyl)amino]ethyl]amino]-3-(phenylmethoxy)-N-[2-(1,3-dioxolan-2-yl)ethyl] propanamide (12.61 g; 0.03 mol). Yield: 46%.

To a solution of 7.50 g of 2-[[2-[(2-aminoethyl)amino] ethyl]amino]-3-(phenylmethoxy)-N-[2-(1,3-dioxolan-2-yl) ethyl]propanamide in 30 mL of 1,2-dichloroethane, 20.64 g of diisopropylethylamine (0.160 mol) and 15.58 g of t-butyl bromoacetate (0.080 mol) are added under inert atmosphere while the temperature is kept between 0° and 5° C. The solution is kept at 15° C. for 24 h. After addition of further t-butyl bromoacetate (4.25 g; 0.022 mol) the solution is kept for 72 h at 15° C. The solution is cooled to 0° C. to favour the precipitation of diisopropylethylamine hydrobromide and then filtered. The filtrate is concentrated, diluted with water (100 mL) and extracted with AcOEt (100 mL). The organic phase, washed with water (2×100 mL), is dried with $Na_2SO_4$ and concentrated to dryness to give a yellow oil. The crude is purified by silica gel chromatography [silica gel 935 g; eluent: AcOEt : n-hexane 1:1 v/v]. Fractions with similar purity are collected end concentrated to dryness to give 5.18 g of the desired product (0.062 mmol). Yield: 34%.

Yield: 16% (calculated on two successive steps)

TLC: silica gel plate 60F 254 Merck

Eluent: AcOEt: n-hexane=1:1

Detector: 0.5% $KMnO_4$ in 0.1N NaOH Rf=0.21

$^1$H-NMR, $^{13}$C-NMR, IR and MS spectra are consistent with the assigned structure.

D) 5,8,11-tris(carboxymethyl)-1-phenyl-4-[(3-oxypropyl) amino]carbonyl-2-oxa-5,8,11-triazatridecan-13-oic acid 67 mL of 1N HCl (0.067 mol) are added to a solution of 14 g of compound C) (0.017 mol) in 280 mL of dioxane. The solution, diluted with 215 mL of $H_2O$, is stirred at 35° C. for 54 h, then at 4° C. for 48 h. After the dioxane evaporation, the aqueous solution is extracted with AcOEt. The organic phase is washed with water then dried with $Na_2SO_4$ and concentrated to dryness. The residue is dissolved in $CH_2Cl_2$ and the solution is concentrated to dryness. The residue is dissolved in $CH_2Cl_2$ and for 1 h, 82 g of trifluoroacetic acid (55.7 mL; 0.719 mol) are added to the solution. The solution is kept at 5° C. for 24 h under inert atmosphere, then is concentrated to dryness. The residue is dissolved in $CH_2Cl_2$ and concentrated to dryness. The process is repeated several times. The resulting oil is dissolved in $CH_2Cl_2$ and extracted with water. The aqueous phase is separated, reduced to a small volume and purified by chromatography through HPLC. 1.5 g of the desired product (2.64 mmol) are obtained.

Yield: 16% m.p.: 100°–102° C. (dec.)

K.F.: 2.27% (w/w)

HPLC: 97% (area %)

Stationary phase: E.Merck Lichrosorb RP-Select B column; 5 mm; 250×4 mm

Mobile phase: Gradient elution;

A=aqueous solution of 0.01M $KH_2PO_4$ and 0.017M $H_3PO_4$

B=A:$CH_3CN$=3:7

| min | % A | % B |
|---|---|---|
| 0 | 90 | 10 |
| 30 | 10 | 90 |
| 40 | 10 | 90 |

Flow: 1.5 mL min–1;
Temperature: 35° C.;
UV detector: 210 nm.
Elemental Analysis

|  | C | H | N | Na | Cl |
|---|---|---|---|---|---|
| % calc.: | 52.81 | 6.38 | 9.85 |  |  |
| % found: | 51.82 | 6.34 | 9.62 | <0.10 | <0.10 |

$^1$H-NMR, $^{13}$C-NMR, IR and MS spectra are consistent with the assigned structure.

EXAMPLE 9

Gadolinium complex of 8,11,14-tris(carboxymethyl)-2,5-dimethyl-6-oxo-7-hydroxymethyl-2,5,8,11,14-pentaazahexadecan-16-oic acid inner salt

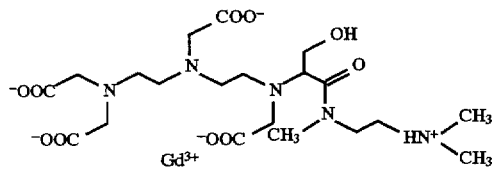

3.5 g Of Pd/C 10% are added to a solution of 21 g of gadolinium complex of 8,11,14-tris-(carboxymethyl)- 2,5-dimethyl-6-oxo-7-[(phenylmethoxy)methyl]-2,5,8,11,14-pentaazahexadecan-16-oic acid (according to EXAMPLE 7) (27.9 mmol) in 300 mL of water and the resulting suspension is kept at 20° C. and under room pressure under hydrogen atmosphere. The suspension is stirred for 24 h, filtered, and added with 10% Pd/C (3.5 g). After 48 h the reaction is completed. The suspension, filtered on paper, Dicalite$^R$, and then on Millipore$^R$ HA 0.45 mm filter, and finally concentrated to dryness to give 17.4 g of the desired product (26.3 mmol).

Yield: 94% m.p.: >200° C. (dec.)

K.F.: 11.66% (w/w)

HPLC: 98.5% (area %)

Stationary phase: E. Merck Lichrosorb RP-18 column; 5 mm; 250×4 mm

Mobile phase: Gradient elution,

A=aqueous solution of N-methylglucamine 0.01M pH 5 buffered with $H_2SO_4$

B=$CH_3CN$

| min | % A | % B |
|---|---|---|
| 0 | 100 | 0 |
| 5 | 100 | 0 |
| 25 | 80 | 20 |

Flow: 1.0 mL, min–1;
Temperature: 50° C.;
UV detector: 195 nm.
Elemental Analysis

|  | C | H | N | Gd |
|---|---|---|---|---|
| % calc.: | 36.30 | 5.18 | 10.58 | 23.70 |
| % found: | 31.77 | 6.05 | 9.27 | 20.81 |

TLC: silica gel plate TLC RP 8
Eluent: $H_2O$
Detector: 0.5% $KMnO_4$ (w/w) in 1N NaOH Rf=0.36
$^1$H-NMR, $^{13}$C-NMR, IR and MS spectra are consistent with the assigned structure.

EXAMPLE 10

Table 1 shows as non-limiting example the osmolality values (mosm/kg) for the products described in examples 1 and 6, compared to Gd-BOPTA/Dimeg (EP 230893), OMNISCAN® and MAGNEVIST®.

| COMPOUND | OSMOLALITY (mosm/kg) (0.25 M) | OSMOLALITY (mosm/kg) (0.5 M) |
|---|---|---|
| EXAMPLE 1 | 257 |  |
| EXAMPLE 6 | 282 | 723 |
| OMNISCAN ® |  | 780 |
| GD-BOPTA/Dimeg | 750 | 1910 |
| MAGNEVIST ® |  | 1940 |

Compared to osmolality values of blood (~0.290 osmol/kg), it is showed that Gd complexes of this invention, show very favourable values, which are completely unexpected in view of known prior-art compounds, characterised by similar structures.

We claim:

1. A compound of formula (I)

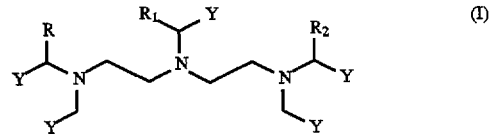

wherein

R, $R_1$, $R_2$ are the same or different and are selected from a hydrogen atom or a A—O—T residue with the proviso that at least one of them is different from hydrogen and in said A—O—T residue:

A is —$CH_2$)m; —$CH_2$—$C(CH_3)_2$—, m is an integer between 1 and 5,

T has one of the following meanings:
   a) is hydrogen,
   b) a straight or branched ($C_1$–$C_{10}$) alkyl group which is unsubstituted or substituted by at least one of 1–6 hydroxy and alkoxy groups, said alkoxy groups are unsubstituted or are substituted by at least one aldehyde, carboxy or amino group of formula —NR₃R₄, a cyclic (C₃–C₆) residue not interrupted or interrupted by at least one N, O, S atom, c) an arylalkyl group comprising 1–2 aryl residues, said aryl residues being unsubstituted or substituted and 1–4 aliphatic carbon atoms, d) a phenyl group, unsubstituted or substituted by at least one halo, hydroxyalkyl, hydroxy, alkoxy, carboxy, aldehyde, amino, mercapto, trifluoromethyl, amido, cyano, thiocyano, nitro, thioalkyl, sulfonic, sulfinic, phosphonic, phosphinic group, or substituted by a straight or branched (C₁–C₈) alkyl, which is unsubstituted or substituted by at least one hydroxy, alkoxy, carboxy, aldehyde, amino group, e) a polyoxaalkyl group comprising 1–10 oxygen atoms and 3–30 carbon atoms, wherein, R₃ and R₄ are the same or different and are
a) hydrogen,
b) a straight or branched (C₁–C₁₀) alkyl group, which is unsubstituted or is substituted by at least one 1–6 hydroxy and alkoxy group and by at least one aldehyde, carboxy, amino group wherein said amino group is neutral, protonated or alkylated in order to supply a quaternary ammonium group, said amino group being unsubstituted or comprising a cyclic, aromatic or non-aromatic residue, said cyclic aromatic or non-aromatic residue being non-interrupted or interrupted by N, O, S atom,
c) a polyoxxaalkyl group comprising 1–10 oxygen atoms and 3–30 carbon atoms, said polyoxaalkyl group being unsubstituted or substituted by a terminal amino group,
d) R₃ and R₄, taken together, form a (C₂–C₈) chain non-interrupted or interrupted by at least one N, O, S atom, or,
e) the —NR₃R₄ group is a guanidine residue of formula

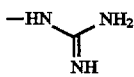

Y is a member selected from the group consisting of —COZ, —PO(OH)Z, —POXZ, —SO₂Z and —SOZ Z independently is a —OH or a —OR₅, or a —NR₃R₄ group wherein R₃ and R₄ are as defined hereinabove, and R₅ is a straight or branched (C₁–C₁₀) alkyl which is unsubstituted or substituted by at least one 1–6 hydroxy and alkoxy groups, X is an aliphatic, aromatic or heteroaromatic group, with the proviso that some or all the acid and basic functions of said compound of formula (I) are either neutral or ionic, and a complexed chelate of said compound of formula (I) with ions of a metal element having atomic number between 20 and 31, 39, 42, 43, 44, 49 and between 57 and 83 and a salt thereof with a physiologically tolerable organic base selected from primary, secondary and tertiary amines or basic aminoacids or with an inorganic base with a cation selected from sodium, potassium, magnesium, calcium or mixtures thereof.

2. A compound of formula (II), according to claim 1

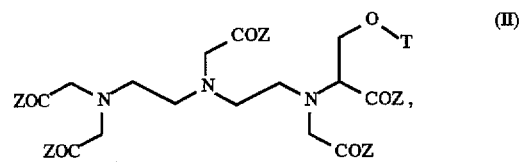

wherein Z and T have the same meanings as in claim 1, and a complexed chelate of said compound of formula (II) with an ion of a metal element having atomic number included between 20 and 31, 39 and between 42 and 44, 49 and between 57 and 83 and a salt thereof with a physiologically tolerable organic base selected from primary, secondary and tertiary amines or basic aminoacids or with an inorganic base with a cation selected from sodium, potassium, magnesium, calcium or mixtures thereof.

3. A compound of formula (III), according to claim 1

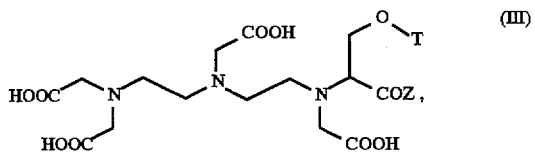

wherein T is a hydrogen atom or a benzyl group and Z is a —NR₃R₄ group selected from: —NH(CH₂)₂O(CH₂)₂OH, —NHCH(CH₂OH)₂, —N(CH₃)(CH₂)₃N(CH₃)₂, —NHCH₂CH₂CHO, —NH(CH₂)₄NHC(NH)NH₂, —NH(CH₂)₃N(CH₃)₂, —NH(CH₂)₂NH₂, —NHC(CH₂CH₂OH)₃,

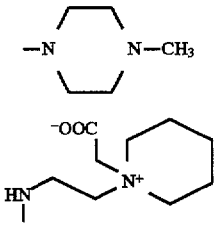

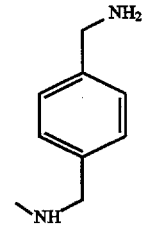

and a complexed chelate of said compound of formula (III) with an ion of a metal element having atomic number included between 20 and 31, 39 and between 42 and 44, 49 and between 57 and 83 and a salts therewith with a physiologically tolerable organic base selected from primary, secondary and tertiary amines or basic aminoacids or an inorganic base with a cation selected from sodium, potassium magnesium, calcium and mixtures thereof.

4. A diagnostic contract agent for nuclear magnetic imaging of at least one of human or animal organs and tissues comprising at least one complexed chelate according to claim 1.

5. A pharmaceutical contrast agent for nuclear magnetic imaging of at least one of human and animal organs and tissues comprising at least one complexed chelate according to claim 1.

6. A compound according to claim 1, selected from:

5,8,11-tris(carboxymethyl)-1-phenyl-4-(4-methyl-1-piperazinyl)carbonyl-2-oxa-5,8,11-triazatridecan-13-oic acid, 1-carboxymethyl-1-[13-carboxy-6,9,12-tris(carboxymethyl)-5-[(phenylmethoxy)methyl]-4-oxo-3,6,9,12-tetraazatridec-1-yl]piperidinium, (4R,S)-5,8,11-tris(carboxymethyl)-1-phenyl-4-[[[2-hydroxy-1-(hydroxymethyl)ethyl]amino]carbonyl]-2-oxa-5,8,11-triazatridecan-13-oic acid, 3,6,9-tris(carboxymethyl)-14-hydroxy-10,13-bis(hydroxymethyl)-11-oxo-3,6,9,12-tetraazatetradecanoic acid, 9,12,15-tris(carboxymethyl)-2,6-dimethyl-7-oxo-8-[(phenylmethoxy)methyl]-2,6,9,12,15-pentaazaeptadecan-17-oic acid, 8,11,14-tris(carboxymethyl)-2,5-dimethyl-6-oxo-7-[(phenylmethoxy)methyl]-2,5,8,11,14-pentaazahexadecan-16-oic acid, 5,8,11-tris(carboxymethyl)-1-phenyl-4-[(3-oxypropyl)amino]carbonyl-2-oxa-5,8,11-triazatridecan-13-oic acid, 8,11,14-tris(carboxymethyl)-2,5-dimethyl-6-oxo-7-hydroxymethyl-2,5,8,11,14-pentaazahexadecan-16-oic acid.

7. A compound according to claim 1, in which the paramagnetic metal ion is selected from $Fe^{(2+)}$, $Fe^{(3+)}$, $Gd^{(3+)}$, $Eu^{(3+)}$, $Dy^{(3+)}$, $La^{(3+)}$, $Yb^{(3+)}$ and $Mn^{(2+)}$.

8. A compound according to claim 1, in which the paramagnetic metal ion is $Gd^{(3+)}$.

9. A compounds according to claim 1, in which the physiologically tolerable organic base is selected from ethanolamine, diethanolamine, morpholine, glucamine, N,N-dimethylglucamine, N-methylglucamine, lysine, arginine, ornithine.

10. The compound 9,12,15-tris(carboxymethyl)-2,6-dimethyl-7-oxo-8-[phenylmethoxy)methyl]-2,6,9,12,15-pentaazaeptadecan-17-oic acid of formula

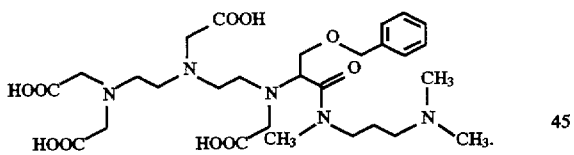

11. A method of nuclear magnetic imaging of at least one of human or animal organs and tissues wherein is utilized a diagnostic formulation comprising at least one compound of formula (I)

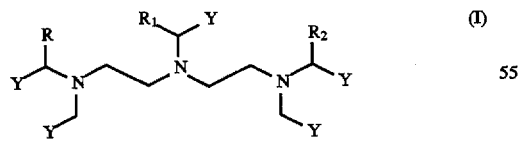 (I)

wherein

R, $R_1$, $R_2$ are the same or different and are selected from a hydrogen atom or a A—O—T residue with the proviso that at least one of them is different from hydrogen and in said A—O—T residue:

A is —(CH$_2$)m; —CH$_2$—C(CH$_3$)$_2$—, m is an integer between 1 and 5,

T has one of the following meanings:

a) is hydrogen, b) a straight or branched ($C_1$-$C_{10}$) alkyl group which is unsubstituted or substituted by at least one of 1–6 hydroxy and alkoxy groups, said alkoxy groups are unsubstituted or are substituted by at least one aldehyde, carboxy or amino group of formula —NR$_3$R$_4$, a cyclic ($C_3$-$C_6$) residue not interrupted or interrupted by at least one N, O, S atom, c) an arylalkyl group comprising 1–2 aryl residues, said aryl residues being unsubstituted or substituted and 1–4 aliphatic carbon atoms, d) a phenyl group, unsubstituted or substituted by at least one halo, hydroxyalkyl, hydroxy, alkoxy, carboxy, aldehyde, amino, mercapto, trifluoromethyl, amido, cyano, thiocyano, nitro, thioalkyl, sulfonic, sulfinic, phosphonic, phosphinic group, or substituted by a straight or branched ($C_1$-$C_8$) alkyl, which is unsubstituted or substituted by at least one hydroxy, alkoxy, carboxy, aldehyde, amino group, e) a polyoxaalkyl group comprising 1–10 oxygen atoms and 3–30 carbon atoms, wherein, $R_3$ and $R_4$ are the same or different and are a) hydrogen, b) a straight or branched ($C_1$-$C_{10}$) alkyl group, which is unsubstituted or is substituted by at least one 1–6 hydroxy and alkoxy group and by at least one aldehyde, carboxy, amino group wherein said amino group is neutral, protonated or alkylated in order to supply a quaternary ammonium group, said amino group being unsubstituted or comprising a cyclic, aromatic or non-aromatic residue, said cyclic aromatic or non-aromatic residue being non-interrupted or interrupted by N, O, S atom, c) a polyoxxaalkyl group comprising 1–10 oxygen atoms and 3–30 carbon atoms, said polyoxaalkyl group being unsubstituted or substituted by a terminal amino group, d) $R_3$ and $R_4$, taken together, form a ($C_2$-$C_8$) chain non-interrupted or interrupted by at least one N, O, S atom, or, e) the —NR$_3$R$_4$ group is a guanidine residue of formula

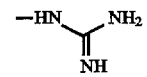

Y is a member selected from the group consisting of —COZ, —PO(OH)Z, —POXZ, —SO$_2$Z and —SOZ Z independently is a —OH or a —OR$_5$, or a —NR$_3$R$_4$ group wherein $R_3$ and $R_4$ are as defined hereinabove, and $R_5$ is a straight or branched ($C_1$-$C_{10}$) alkyl which is unsubstituted or substituted by at least one 1–6 hydroxy and alkoxy groups, X is an aliphatic, aromatic or heteroaromatic group, with the proviso that some or all the acid and basic functions of said compound of formula (I) are either neutral or ionic, and a complexed chelate of said compound of formula (I) with ions of a metal element having atomic number between 20 and 31, 39, 42, 43, 44, 49 and between 57 and 83 and a salt thereof with a physiologically tolerable organic base selected from primary, secondary and tertiary amines or basic aminoacids or with an inorganic base with a cation selected from sodium, potassium, magnesium, calcium or mixtures thereof.

* * * * *